US00PP27265P2

(12) United States Plant Patent
Oliver

(10) Patent No.: US PP27,265 P2
(45) Date of Patent: Oct. 11, 2016

(54) ***PHLOX* PLANT NAMED 'SOLAR FLARE'**

(50) Latin Name: ***Phlox carolina* ssp. *carolina*×*Phlox carolina* ssp. *angusta***
Varietal Denomination: Solar Flare

(71) Applicant: Charles G. Oliver, Scottdale, PA (US)

(72) Inventor: Charles G. Oliver, Scottdale, PA (US)

( * ) Notice: Subject to any disclaimer, the term of this patent is extended or adjusted under 35 U.S.C. 154(b) by 91 days.

(21) Appl. No.: 14/544,218

(22) Filed: Dec. 9, 2014

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Annette Para
(74) *Attorney, Agent, or Firm* — C. A. Whealy

(57) ABSTRACT

A new and distinct *Phlox* plant named 'Solar Flare', characterized by its upright and mounding plant form; vigorous growth habit; freely basal branching habit; early and freely flowering habit; large rounded inflorescences with white and red purple-colored flowers; and resistance to Powdery Mildew.

2 Drawing Sheets

Botanical designation: *Phlox carolina* ssp. *carolina*× *Phlox carolina* ssp. *angusta.*

Cultivar denomination: 'SOLAR FLARE'.

BACKGROUND OF THE INVENTION

The present invention relates to a new and distinct *Phlox* plant, botanically known as *Phlox carolina* ssp. *carolina*× *Phlox carolina* ssp. *angusta* and hereinafter referred to by the name 'Solar Flare'.

The new *Phlox* plant is a product of a planned breeding program conducted by the Inventor in Upper Tyrone Township, Pa. The objective of the breeding program is to create new vigorous *Phlox* plants with early flowering habit, attractive leaf and flower coloration and resistance to Powdery Mildew.

The new *Phlox* plant originated from a cross-pollination conducted by the Inventor in July, 2007 of *Phlox carolina* ssp. *carolina* 'Minnie Pearl', not patented, as the female, or seed, parent with *Phlox carolina* ssp. *angusta* 'Gypsy Love', not patented, as the male, or pollen, parent. The new *Phlox* plant was discovered and selected by the Inventor as a single flowering plant within the progeny of the stated cross-pollination in a controlled environment in Upper Tyrone Township, Pa. in June, 2008.

Asexual reproduction of the new *Phlox* plant by vegetative stem cuttings in a controlled greenhouse environment in Upper Tyrone Township, Pa. since September, 2008 has shown that the unique features of this new *Phlox* plant are stable and reproduced true to type in successive generations.

SUMMARY OF THE INVENTION

Plants of the new *Phlox* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Solar Flare'. These characteristics in combination distinguish 'Solar Flare' as a new and distinct *Phlox* plant:

1. Upright and mounding plant form.
2. Vigorous growth habit.
3. Freely basal branching habit.
4. Early and freely flowering habit.
5. Large rounded inflorescences with white and red purple-colored flowers.
6. Resistance to Powdery Mildew.

Plants of the new *Phlox* differ from plants of the female parent, 'Minnie Pearl', in the following characteristics:

1. Plants of the new *Phlox* are taller and denser than plants of 'Minnie Pearl'.
2. Plants of the new *Phlox* have shorter internodes than plants of 'Minnie Pearl'.
3. Plants of the new *Phlox* and 'Minnie Pearl' differ in stem color.
4. Plants of the new *Phlox* have larger leaves than plants of 'Minnie Pearl'.
5. Plants of the new *Phlox* have larger inflorescences with more flowers per inflorescence than plants of 'Minnie Pearl'.
6. Inflorescences of plants of the new *Phlox* are rounded in shape whereas inflorescences of plants of 'Minnie Pearl' are flat-topped.
7. Plants of the new *Phlox* and 'Minnie Pearl' differ in flower color as plants of 'Minnie Pearl' have white-colored flowers.

Plants of the new *Phlox* differ from plants of the male parent, 'Gypsy Love', in the following characteristics:

1. Plants of the new *Phlox* have shorter leaves than plants of 'Gypsy Love'.
2. Plants of the new *Phlox* have larger inflorescences than plants of 'Gypsy Love'.
3. Plants of the new *Phlox* have larger flowers than plants of 'Gypsy Love'.
4. Plants of the new *Phlox* and 'Gypsy Love' differ slightly in flower color.

Plants of the new *Phlox* can be compared to plants of *Phlox maculata* 'Flower Power', disclosed in U.S. Plant Pat.

No. 17,551. In side-by-side comparisons, plants of the new *Phlox* and 'Flower Power' differed in the following characteristics:

1. Plants of the new *Phlox* had longer and narrower leaves than plants of 'Flower Power'.
2. Inflorescences of plants of the new *Phlox* were rounded in shape whereas inflorescences of plants of 'Flower Power' were cylindrical in shape.
3. Plants of the new *Phlox* and 'Flower Power' differed slightly in flower color.

Plants of the new *Phlox* can also be compared to plants of *Phlox paniculata* 'Blushing Shortwood', disclosed in U.S. Plant Pat. No. 20,331. In side-by-side comparisons, plants of the new *Phlox* and 'Blushing Shortwood' differed in the following characteristics:

1. Plants of the new *Phlox* had smaller leaves than plants of 'Blushing Shortwood'.
2. Plants of the new *Phlox* flowered earlier than plants of 'Blushing Shortwood'.
3. Plants of the new *Phlox* and 'Blushing Shortwood' differed in flower color as plants of 'Blushing Shortwood' had white and pale purple bi-colored flowers.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of typical flowering plants of 'Solar Flare'.

The photograph at the top of the sheet is a close-up view of a typical flowering plant of 'Solar Flare'.

DETAILED BOTANICAL DESCRIPTION

The aforementioned photographs and following observations, measurements and values describe plants grown during the spring and summer in one-gallon containers in a polyethylene-covered greenhouse and an outdoor nursery in Upper Tyrone Township, Pa. and under cultural practices typical of *Phlox* production. During the production of the plants, day temperature averaged 26° C. and night temperatures averaged 15° C. Plants were two years old when the photographs and description were taken. In the following description, color references are made to The Royal Horticultural Society Colour Chart, 1995 Edition, except where general terms of ordinary dictionary significance are used.

Botanical classification: *Phlox carolina* ssp. *carolina*×*Phlox carolina* ssp. *angusta* 'Solar Flare'.

Parentage:

*Female, or seed, parent.*—*Phlox carolina* ssp. *carolina* 'Minnie Pearl', not patented.

*Male, or pollen, parent.*—*Phlox carolina* ssp. *angusta* 'Gypsy Love', not patented.

Propagation:

*Type.*—By stem cuttings.

*Time to initiate roots, summer.*—About three weeks at night temperatures about 15° C. and day temperatures about 26° C.

*Time to produce a rooted plant, summer.*—About six weeks at night temperatures about 15° C. and day temperatures about 26° C.

*Root description.*—Medium in thickness, fibrous; white in color.

*Rooting habit.*—Freely branching; medium density.

Plant description:

*Plant and growth habit.*—Herbaceous perennial; upright and mounding plant habit, columnar; vigorous growth habit; freely basal branching habit with about six to ten primary laterals developing per plant.

*Plant height.*—About 60 cm.

*Plant width (spread).*—About 45 cm.

*Lateral branches.*—Length: About 60 cm. Diameter: About 2.5 mm. Internode length: About 2.5 cm; distally, about 6 cm. Strength: Strong. Texture: Sparsely pubescent. Color: Close to 144B, mottled and streaked with close to 184D.

Leaf description:

*Arrangement.*—Opposite, simple; sessile.

*Length.*—About 6.5 cm to 10.5 cm.

*Width.*—About 4 mm to 16 mm.

*Shape.*—Lanceolate.

*Apex.*—Acute.

*Base.*—Abruptly tapering.

*Margin.*—Entire.

*Texture, upper and lower surfaces.*—Glabrous; thick; waxy.

*Venation pattern.*—Pinnate.

*Color.*—Developing and fully expanded leaves, upper surface: Close to 139B; venation, close to 139B. Developing and fully expanded leaves, lower surface: Close to 139C; venation, close to 139C.

Flower description:

*Flower form and flowering habit.*—Single rotate and salverform flowers arranged in terminal compound panicles; panicles rounded in shape; freely flowering habit with about 80 to 100 flowers developing per inflorescence; flowers face upright to mostly outwardly.

*Fragrance.*—Faintly fragrant; sweet.

*Natural flowering season.*—Early flowering habit, plants begin flowering about six weeks after planting; plants flowering continuously from early June to mid-July in Pennsylvania.

*Postproduction longevity.*—Flowers last about seven to ten days on the plant and as a cut flower; flowers not persistent.

*Flower buds.*—Height: About 2.6 cm. Diameter: About 3.5 mm. Shape: Elongated oblong: Color: Close to 74C.

*Inflorescence height.*—About 10 cm to 12 cm.

*Inflorescence diameter.*—About 9 cm to 12 cm.

*Flower diameter.*—About 2.5 cm.

*Flower depth.*—About 2.5 cm.

*Flower throat diameter.*—About 1.8 mm.

*Flower tube length.*—About 2.4 cm.

*Flower tube diameter, at base.*—About 2 mm.

*Petals.*—Quantity per flower and arrangement: Typically five in a single whorl; petals fused at the base into a narrow tube. Lobe length: About 1.1 cm. Lobe width: About 1.2 cm. Shape: Rhomboidal. Apex: Obtuse. Margin: Entire. Texture: Petal lobes, upper and lower surfaces: Smooth, glabrous. Throat: Smooth, glabrous Tube: Smooth, glabrous. Color: Developing petal lobes, upper surface: Close to 155D; towards the base, shaded with close to 74B.

Developing petal lobes, lower surface: Close to 155D shaded with close to 74D. Fully expanded petal lobes, upper surface: Close to 155D; towards the base, shaded with close to 74B. Fully expanded petal lobes, lower surface: Close to 155D; towards the base shaded with close to 74D. Flower throat: Close to 74B. Flower tube: Close to 74D.

*Sepals*.—Quantity per flower and arrangement: Typically five in a single whorl, fused towards the base into a slender tube. Length: About 9 mm. Width: About 1.5 mm. Shape: Lanceolate. Apex: Acute. Margin: Entire, membraneous. Texture, upper and lower surfaces: Smooth, glabrous. Color, upper surface: Close to 145B. Color, lower surface: Close to 145B shaded with close to 70B.

*Peduncles*.—Length: About 3 cm. Diameter: About 2 mm. Angle: Erect. Strength: Strong. Texture: Pilose. Color: Close to 145B with mottling, close to 59B.

*Pedicels*.—Length: About 4 mm to 5 mm. Diameter: About 0.5 mm. Angle: About 30° from peduncle axis. Strength: Strong. Texture: Pilose. Color: Close to 145B.

*Reproductive organs*.—Stamens: Quantity per flower: Typically five. Filament length: About 2 mm. Anther shape: Oval. Anther length: About 2 mm. Anther color: Close to 17C. Pollen amount: Scarce. Pollen color: Close to 17C. Pistils: Quantity per flower: One. Pistil length: About 2.5 cm. Stigma shape: Tri-parted. Stigma color: Close to 154C. Style length: About 2.3 cm. Style color: Close to 154C. Ovary color: Close to 145B.

*Seeds and fruits*.—Seed and fruit development have not been observed on plants of the new *Phlox* plant.

Disease & pest resistance: Plants of the new *Phlox* have been observed to be resistant to Powdery Mildew. Plants of the new *Phlox* have not been observed to be resistant to pests and other pathogens common to *Phlox* plants.

Garden performance: Plants of the new *Phlox* have been observed to have good garden performance and tolerate rain and wind and to temperatures ranging from about −30° C. to 45° C.

It is claimed:

1. A new and distinct *Phlox* plant named 'Solar Flare' as illustrated and described.

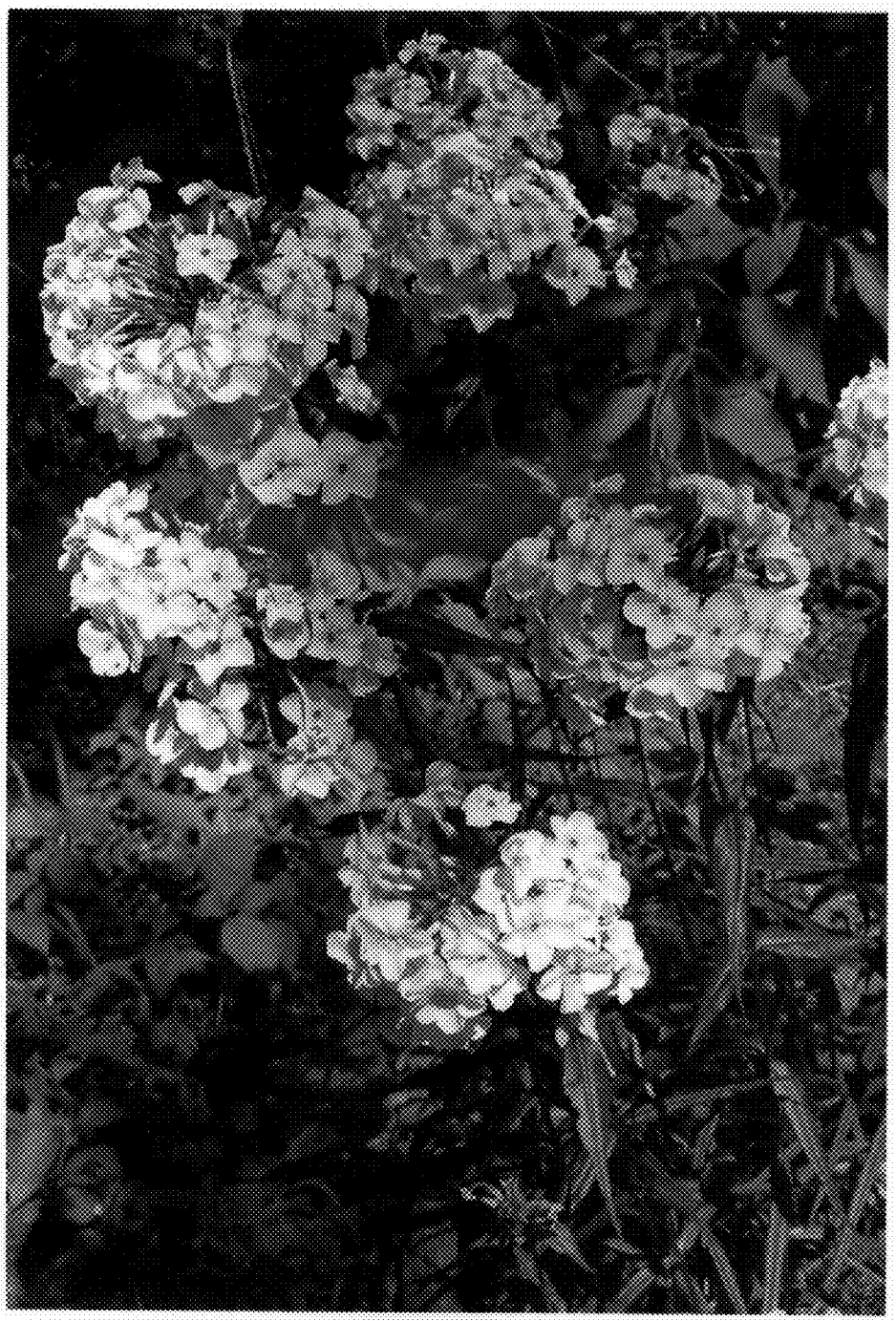

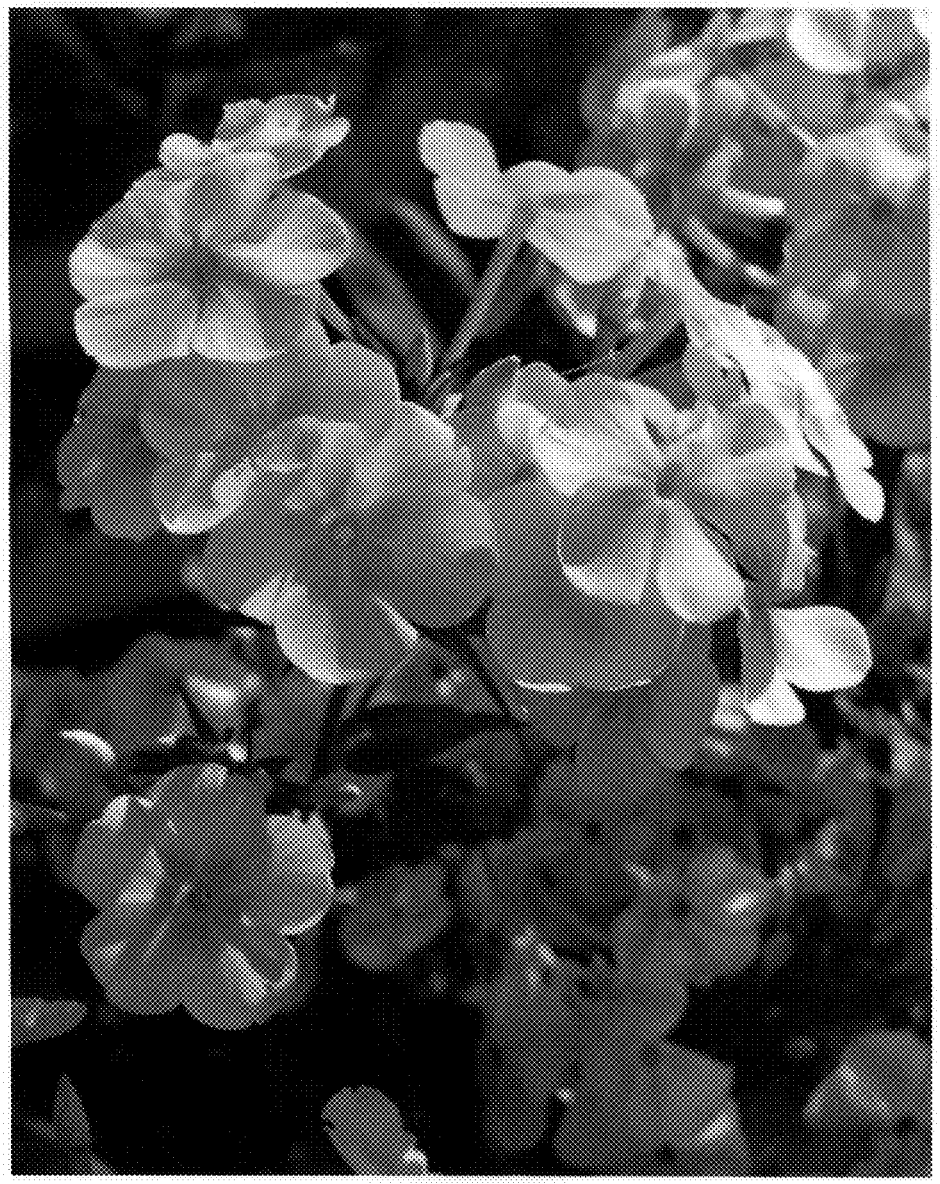

* * * * *